(12) United States Patent
Shirai et al.

(10) Patent No.: US 11,174,269 B2
(45) Date of Patent: Nov. 16, 2021

(54) METHOD FOR PRODUCING 1,2,4,5-CYCLOHEXANETETRACARBOXYLIC DIANHYDRIDE

(71) Applicant: MITSUBISHI GAS CHEMICAL COMPANY, INC., Chiyoda-ku (JP)

(72) Inventors: Shinyo Shirai, Okayama (JP); Tatsuyuki Kumano, Okayama (JP); Shinya Saito, Okayama (JP)

(73) Assignee: MITSUBISHI GAS CHEMICAL COMPANY, INC., Chiyoda-ku (JP)

(*) Notice: Subject to any disclaimer, the term of this patent is extended or adjusted under 35 U.S.C. 154(b) by 0 days.

(21) Appl. No.: 16/496,697

(22) PCT Filed: Mar. 22, 2018

(86) PCT No.: PCT/JP2018/011331
§ 371 (c)(1),
(2) Date: Sep. 23, 2019

(87) PCT Pub. No.: WO2018/180854
PCT Pub. Date: Oct. 4, 2018

(65) Prior Publication Data
US 2020/0031841 A1    Jan. 30, 2020

(30) Foreign Application Priority Data

Mar. 29, 2017  (JP) .............................. JP2017-065899
Mar. 29, 2017  (JP) .............................. JP2017-065907

(51) Int. Cl.
 *C07D 493/06*    (2006.01)
 *C07D 493/04*    (2006.01)

(52) U.S. Cl.
 CPC ................................. *C07D 493/04* (2013.01)

(58) Field of Classification Search
 CPC .................................................. C07D 493/06
 See application file for complete search history.

(56) References Cited

U.S. PATENT DOCUMENTS

| 6,927,306 B2* | 8/2005 | Zaima | ................. | C07D 307/89 |
| | | | | 562/400 |
| 2003/0149297 A1 | 8/2003 | Zaima | | |
| 2020/0039999 A1* | 2/2020 | Shirai | ................. | C07D 493/04 |

FOREIGN PATENT DOCUMENTS

| CN | 103992330 | 8/2014 |
| CN | 104926649 | 9/2015 |
| JP | 2003-286222 A | 10/2003 |
| JP | 2006-83080 A | 3/2006 |
| JP | 2006-124313 A | 5/2006 |

OTHER PUBLICATIONS

Hixson, A. W.; Crowell, J. H. "Dependence of Reaction Velocity upon Surface and Agitation." Industrial and Engineering Chemistry (1931), vol. 23 No. 8, pp. 923-931 (Year: 1931).*
International Search Report dated May 29, 2018 in PCT/JP2018/011331 filed Mar. 22, 2018.

* cited by examiner

*Primary Examiner* — John S Kenyon
(74) *Attorney, Agent, or Firm* — Oblon, McClelland, Maier & Neustadt, L.L.P.

(57) ABSTRACT

An object of the present invention is to provide a method for producing 1,2,4,5-cyclohexanetetracarboxylic dianhydride, which is capable of stably achieving a high dehydration rate. The method for producing 1,2,4,5-cyclohexanetetracarboxylic dianhydride of the present invention is a method for producing 1,2,4,5-cyclohexanetetracarboxylic dianhydride by subjecting 1,2,4,5-cyclohexanetetracarboxylic acid to a dehydration reaction in a slurry state in the presence of a dehydrating agent, wherein an average particle size of the 1,2,4,5-cyclohexanetetracarboxylic acid is 20 μm or more.

10 Claims, No Drawings

METHOD FOR PRODUCING 1,2,4,5-CYCLOHEXANETETRACARBOXYLIC DIANHYDRIDE

TECHNICAL FIELD

The present invention relates to a method for producing 1,2,4,5-cyclohexanetetracarboxylic dianhydride.

BACKGROUND ART

Alicyclic acid anhydrides have been used as starting materials for functional polyimides and functional epoxy resins Among such acid anhydrides, 1,2,4,5-cyclohexanetetracarboxylic dianhydride is used as a starting material for polyimide resins that exhibit particularly good heat resistance, solvent solubility and thermoplasticity as well as low water absorbability, dimensional stability and the like.

For the synthesis of a polyimide, an acid anhydride and a diamine are desirably used in equivalent amounts because the molecular weight of the polyimide does not sufficiently increase when the molar balance of the acid anhydride and the diamine is lost. Also, impurities contained in the diamine and the acid anhydride cause the loss of molar balance. Accordingly, the acid anhydride as a starting material is required to have high purity.

An acid anhydride is known to be obtained by subjecting a hydrogenated aromatic polycarboxylic acid to a dehydration reaction. For example, 1,2,4,5-cyclohexanetetracarboxylic dianhydride is produced by cyclodehydration of 1,2,4,5-cyclohexanetetracarboxylic acid. A method involving a heat treatment or a method involving a dehydrating agent is commonly used to synthesize a cyclic acid anhydride by dehydrating and ring-closing the carboxy groups adjacently bonded to the 6-membered ring of a hydrogenated aromatic polycarboxylic acid. An acid anhydride such as acetic anhydride or propionic anhydride is used as a dehydrating agent.

A method involving thermal reflux using acetic anhydride is known as a method for cyclodehydrating 1,2,4,5-cyclohexanetetracarboxylic acid (see PTL1).

CITATION LIST

Patent Literature

PTL1: JP 2003-286222 A

SUMMARY OF INVENTION

Technical Problem

PTL1 discloses that a hydrogenated aromatic polycarboxylic acid is dehydrated by a method involving acetic anhydride as a dehydrating agent, but the method has the following problem: the high dehydration rate set forth in PTL1 cannot be reproduced depending on the conditions.

Moreover, in the method for producing a hydrogenated aromatic polycarboxylic anhydride described in PTL1, the particle size of the hydrogenated aromatic polycarboxylic anhydride is not taken into consideration.

An object of the present invention is to provide a method for producing 1,2,4,5-cyclohexanetetracarboxylic dianhydride, which is capable of stably achieving a high dehydration rate.

Solution to Problem

As a result of diligent research to solve the above problem, the present inventors found that 1,2,4,5-cyclohexanetetracarboxylic dianhydride having a high dehydration rate can be stably obtained by using 1,2,4,5-cyclohexanetetracarboxylic acid having a specific average particle size as a starting material, and accomplished the present invention. The present invention provides [1] to [13] below.

[1] A method for producing 1,2,4,5-cyclohexanetetracarboxylic dianhydride by subjecting 1,2,4,5-cyclohexanetetracarboxylic acid to a dehydration reaction in a slurry state in the presence of a dehydrating agent, wherein an average particle size of the 1,2,4,5-cyclohexanetetracarboxylic acid is 20 μm or more (preferably 25 μm or more and more preferably 30 μm, and may be 1000 μm or less, 500 μm or less, 300 μm or less, and 100 μm or less).

[2] The method according to [1], wherein in the 1,2,4,5-cyclohexanetetracarboxylic acid, a proportion of particles having a particle size of 10 μm or less is 20% by number or less (preferably 15% by number or less and more preferably 10% by number or less).

[3] The method according to [1] or [2], wherein in the 1,2,4,5-cyclohexanetetracarboxylic acid, a proportion of particles having a particle size of 40 μm or more is 20% by number or more (preferably 25% by number or more).

[4] The method according to any one of [1] to [3], wherein in the 1,2,4,5-cyclohexanetetracarboxylic acid, a proportion of particles having a particle size of 20 μm or more is 35% by number or more (preferably 45% by number or more, more preferably 55% by number or more, even more preferably 65% by number or more, and further preferably 75% by number or more).

[5] The method according to any one of [1] to [4], wherein a dehydration rate of the 1,2,4,5-cyclohexanetetracarboxylic acid is 98% or more.

[6] The method according to any one of [1] to [5], wherein a reaction temperature of the dehydration reaction is 80 to 150° C. (preferably 90° C. or more and more preferably 95° C. or more, and preferably 140° C. or less, more preferably 130° C. or less, and even more preferably 120° C. or less).

[7] The method according to any one of [1] to [6], wherein the dehydrating agent is acetic anhydride.

[8] The method according to [7], wherein the acetic anhydride is used in an amount of 2.0 to 100 moles (preferably 2.5 moles or more, more preferably 3 moles or more and even more preferably 4 moles or more, and preferably 75 moles or less, more preferably 50 moles or less and even more preferably 25 moles or less) per mole of the 1,2,4,5-cyclohexanetetracarboxylic acid.

[9] The method according to any one of [1] to [8], wherein the dehydration reaction of the 1,2,4,5-cyclohexanetetracarboxylic acid is carried out in the presence of the dehydrating agent and a solvent.

[10] The method according to [9], wherein the solvent is acetic acid.

[11] A method for producing 1,2,4,5-cyclohexanetetracarboxylic acid crystals, wherein the method comprises the following step 1 and step 2 in this order, and a concentration of a concentrate obtained in step 1 is 29% by mass or more and 34% by mass or less:
Step 1: Concentrating an aqueous solution comprising 1,2,4,5-cyclohexanetetracarboxylic acid to obtain a concentrate; and
Step 2: Cooling the concentrate.

[12] The method according to [11], wherein purity of the 1,2,4,5-cyclohexanetetracarboxylic acid crystals is 99% or more.

[13] The method according to [11] or [12], wherein, in step 1, the aqueous solution is concentrated until the 1,2,4,5-cyclohexanetetracarboxylic acid crystals precipitate.

Advantageous Effects of Invention

According to the present invention, a method for producing 1,2,4,5-cyclohexanetetracarboxylic dianhydride, which is capable of stably achieving a high dehydration rate, can be provided.

DESCRIPTION OF EMBODIMENTS

The present invention will be described in reference to embodiments below. In the following description, "A to B" indicating a numerical range denotes "A or more and B or less" (in the case of A<B) or "A or less and B or more" (in the case of A>B). That is, "A to B" denotes a numerical range including end points A and B.

Also, part by mass and % by mass are synonymous with part by weight and % by weight, respectively.

The method for producing cyclohexanetetracarboxylic dianhydride of the present invention is a method for producing 1,2,4,5-cyclohexanetetracarboxylic dianhydride (hereinafter also simply referred to as "cyclohexanetetracarboxylic dianhydride") by subjecting 1,2,4,5-cyclohexanetetracarboxylic acid (hereinafter also simply referred to as "cyclohexanetetracarboxylic acid") to a dehydration reaction in a slurry state in the presence of a dehydrating agent, wherein an average particle size of the 1,2,4,5-cyclohexanetetracarboxylic acid is 20 μm or more.

In PTL1, the particle size of the cyclohexanetetracarboxylic acid as a starting material is not taken into consideration.

The present inventors found that 1,2,4,5-cyclohexanetetracarboxylic dianhydride having a high dehydration rate can be stably obtained by using the cyclohexanetetracarboxylic acid having an average particle size of 20 μm or more as a starting material.

In the following description, the dehydrating agent and the optionally used solvent may be collectively referred to as a "solution."

In the reaction system, either the cyclohexanetetracarboxylic acid as a starting material or the cyclohexanetetracarboxylic dianhydride as a product do not completely dissolve. Accordingly, the reaction system proceeds in a slurry state from the beginning to the end.

It is inferred that, in the above reaction system, the water exchange reaction between cyclohexanetetracarboxylic acid and acetic anhydride primarily proceeds through the reaction between part of the cyclohexanetetracarboxylic acid dissolved in a solution and a dehydrating agent.

In this case, it is considered that, in order to prompt the dissolution stage of cyclohexanetetracarboxylic acid, a starting material having a small particle size and thus having a large area of contact with the solvent is advantageous, and therefore a smaller particle size of the starting material is more advantageous for the rate of the entire reaction.

However, as a result of diligent research, the present inventors surprisingly found that when a starting material having a larger particle size is used, the reaction proceeds at a higher dehydration rate.

Although the details of the mechanism that provides the above effect are not clear, part of the mechanism is conjectured as follows.

As described above, the cyclohexanetetracarboxylic acid as a starting material and the cyclohexanetetracarboxylic dianhydride as a product after a dehydration reaction (also referred to as an anhydration reaction) both have poor solubility in a dehydrating agent and a solvent, and the dehydration reaction proceeds in a slurry state. More specifically, it is considered that part of the cyclohexanetetracarboxylic acid dissolves in a solution, undergoes a dehydration reaction, and forms cyclohexanetetracarboxylic dianhydride, but since the produced cyclohexanetetracarboxylic dianhydride also has poor solubility in the solution, the produced cyclohexanetetracarboxylic dianhydride precipitates upon production. It is conjectured that when cyclohexanetetracarboxylic dianhydride precipitates, the cyclohexanetetracarboxylic acid as a starting material in the case of having a small particle size is likely to be incorporated into the precipitates when the cyclohexanetetracarboxylic dianhydride as a product precipitates, resulting in a poor dehydration rate.

On the other hand, it is conjectured that due to the use of the cyclohexanetetracarboxylic acid having an average particle size as large as 20 μm or more as a starting material, the amount of cyclohexanetetracarboxylic acid incorporated is suppressed when the cyclohexanetetracarboxylic dianhydride as a product precipitates, resulting in a high dehydration rate. Accordingly, a high dehydration rate is stably obtained by using cyclohexanetetracarboxylic acid having a specific particle size as a starting material.

Such a reaction mechanism is a phenomenon specific to cyclohexanetetracarboxylic acid having poor solubility in a solution and undergoing a dehydration reaction in a slurry state, and is an issue specific thereto that does not occur in the dehydration reaction of other polycarboxylic acids having high solubility in a solution and undergoing a dehydration reaction in a homogeneous system.

In the method for producing cyclohexanetetracarboxylic anhydride of the present invention, the following dehydration reaction occurs.

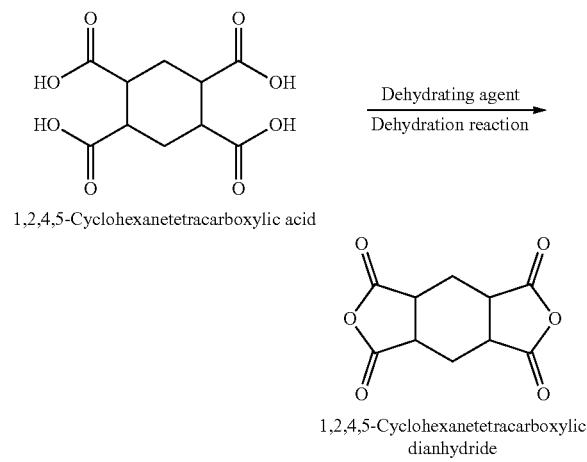

1,2,4,5-Cyclohexanetetracarboxylic acid 1,2,4,5-Cyclohexanetetracarboxylic dianhydride

[Formula 1]

<1,2,4,5-Cyclohexanetetracarboxylic Acid>

In the present invention, 1,2,4,5-cyclohexanetetracarboxylic acid is not particularly limited. A commercially available product may be purchased, or 1,2,4,5-cyclohexanetetracarboxylic acid may be produced by nuclear hydrogenation of pyromellitic acid.

(Method for Producing 1,2,4,5-Cyclohexanetetracarboxylic Acid by Nuclear Hydrogenation of Pyromellitic Acid)

The method for producing 1,2,4,5-cyclohexanetetracarboxylic acid by nuclear hydrogenation of pyromellitic acid is not particularly limited. Examples include, but are not limited to, a method in which pyromellitic acid is dissolved or suspended in a reaction solvent and hydrogenated in the presence of a catalyst at a hydrogen partial pressure of 1.0 to 15 MPa at a reaction temperature of 30 to 80° C. wherein a supported catalyst containing rhodium as well as palladium and/or platinum supported on a carbon carrier is used in a specific amount as the catalyst, as described in WO 2010/010869; and a method in which pyromellitic acid is hydrogenated at a hydrogen partial pressure of 1 MPa or more in the presence of a catalyst containing a noble metal composed of rhodium or palladium or both in a proportion of 0.5 to 10 parts by mass per 100 parts by mass of pyromellitic acid, as described in PTL1.

After the nuclear hydrogenation reaction, for example, the catalyst is separated by filtration at a temperature similar to the reaction temperature, the filtrate is cooled to room temperature, the precipitated solids are separated by filtration, the filtered solids are dried, and thereby 1,2,4,5-cyclohexanetetracarboxylic acid can be obtained. Also, the reaction solvent is distilled off from the filtrate to concentrate the filtrate, the precipitated solids are separated by filtration, then the hydrogenated product hydride of pyromellitic acid is crystallized by being cooled, concentrated, or the like, the crystals thereof are subjected to solid-liquid separation, and thereby high-purity 1,2,4,5-cyclohexanetetracarboxylic acid can be obtained.

In the present invention, crystals of 1,2,4,5-cyclohexanetetracarboxylic acid (1,2,4,5-cyclohexanetetracarboxylic acid crystals) used as a starting material are preferably produced from an aqueous solution containing 1,2,4,5-cyclohexanetetracarboxylic acid by the following method.

That is, in the present invention, the method for producing 1,2,4,5-cyclohexanetetracarboxylic acid crystals preferably comprises the following step 1 and step 2 in this order, wherein a concentration of the concentrate obtained in step 1 is 29% by mass or more and 34% by mass or less:

Step 1: Concentrating an aqueous solution comprising 1,2,4,5-cyclohexanetetracarboxylic acid to obtain a concentrate; and Step 2: Cooling the concentrate.

To date, a batch-wise crystal precipitation method is used in which a concentrate that has been concentrated to a specific concentration is cooled to precipitate and purify crystals.

At that time, a high concentration is desired from the viewpoint of improving the yield, but, on the other hand, an excessively high concentration is not intended from the viewpoint of the purity of the resulting crystals.

As a result of having conducted diligent research, the present inventors surprisingly found that an increased concentration does not deteriorate quality (purity) and improves yield when 1,2,4,5-cyclohexanetetracarboxylic acid crystals are precipitated from an aqueous solution containing 1,2,4,5-cyclohexanetetracarboxylic acid.

The aqueous solution containing 1,2,4,5-cyclohexanetetracarboxylic acid used in step 1 above is suitably, but is not limited to, a reaction solution obtained by the nuclear hydrogenation reaction of pyromellitic acid.

In the present invention, the concentration of the concentrate obtained in step 1 is 29% by mass or more and 34% by mass or less. Here, the "concentration of the concentrate" refers to a value (% by mass) obtained by dividing the mass of 1,2,4,5-cyclohexanetetracarboxylic acid contained in the concentrate by the total mass of the concentrate. Part of the 1,2,4,5-cyclohexanetetracarboxylic acid in the concentrate may be present in a solid state due to precipitation or the like.

The concentration of the concentrate obtained in step 1 is preferably 29.5% by mass or more and more preferably 30% by mass or more.

In step 1, the aqueous solution is preferably concentrated until part of the 1,2,4,5-cyclohexanetetracarboxylic acid precipitates. That is, the concentration of the concentrate is preferably increased so as to be higher than the saturation solubility (the concentration (% by mass) of the saturated aqueous solution) at the concentration temperature. Concentrating the aqueous solution until part of the 1,2,4,5-cyclohexanetetracarboxylic acid precipitates enables 1,2,4,5-cyclohexanetetracarboxylic acid crystals to be obtained in a good yield without deteriorating quality (purity), and is thus preferable. However, a concentration of the concentrate in step 1 exceeding 34% by mass is likely to deteriorate quality.

Here, the saturation solubility of 1,2,4,5-cyclohexanetetracarboxylic acid in water is as follows.

TABLE 1

| Temperature (° C.) | Saturation solubility* |
|---|---|
| 88.2 | 29.6 |
| 98.3 | 33.1 |
| 100 | 33.7 |

*"Saturation solubility" in Table 1 means the concentration (% by mass) of a saturated aqueous solution of 1,2,4,5-cyclohexanetetracarboxylic acid. That is, it means the amount (g) of 1,2,4,5-cyclohexanetetracarboxylic acid contained in 100 g of a saturated aqueous solution of 1,2,4,5-cyclohexanetetracarboxylic acid.

The temperature of the concentrate in concentrating in step 1 is preferably 50° C. or more, more preferably 80° C. or more, and even more preferably 90° C. or more from the viewpoint of facilitating concentration and from the viewpoint of increasing the difference of the saturation solubility when cooled, and is preferably 100° C. or less from the viewpoint of enabling concentration at normal pressure.

Concentration may be carried out under reduced pressure, and the pressure is not particularly limited. When concentration (distilling off the solvent) is carried out under reduced pressure, the pressure is preferably 30 to 450 hPa, more preferably 70 to 300 hPa, and even more preferably 100 to 200 hPa.

At the time of concentration, the aqueous solution is preferably concentrated while being stirred from the viewpoint of suppressing temperature distribution in the concentrate and preventing bumping.

The stirring speed when the aqueous solution is concentrated is not particularly limited as long as the solution is sufficiently stirred, and the stirring speed is preferably 50 rpm to 1000 rpm, more preferably 100 rpm to 800 rpm, and even more preferably 200 rpm to 600 rpm.

The cooling temperature in step 2 is preferably 40° C. or less, more preferably 30° C. or less, and even more preferably 20° C. or less from the viewpoint of obtaining a good yield, and the temperature is preferably 0° C. or more, more preferably 3° C. or more, and even more preferably 5° C. or more from the viewpoint of handleability.

The cooling rate in step 2 is preferably 1° C./h or more, more preferably 5° C./h or more, and even more preferably 10° C./h or more, and is preferably 40° C./h or less, more preferably 30° C./h or less, and even more preferably 20° C./h or less.

In step 2, the concentrate may be cooled in a stationary state or in a stirred state. The concentrate is preferably cooled in a stationary state from the viewpoint of obtaining large crystals, and is preferably cooled in a stirred state from the viewpoint of productivity.

The stirring speed is not particularly limited as long as the liquid is sufficiently stirred during cooling and retaining, and is preferably 50 rpm to 1000 rpm, more preferably 100 rpm to 800 rpm, and even more preferably 200 rpm to 600 rpm.

Crystals of 1,2,4,5-cyclohexanetetracarboxylic acid precipitated through step 2 are separated by a commonly used method such as filtration. The resulting 1,2,4,5-tetracarboxylic acid crystals (1,2,4,5-cyclohexanetetracarboxylic acid) may be washed with water at low temperature or with an organic solvent or the like in which 1,2,4,5-cyclohexanetetracarboxylic acid is insoluble or poorly soluble.

Moreover, it is preferable to dry the resulting 1,2,4,5-cyclohexanetetracarboxylic acid crystals.

The purity of 1,2,4,5-cyclohexanetetracarboxylic acid crystals produced through step 1 and step 2 described above is preferably 98% by mass or more, more preferably 98.5% by mass or more, even more preferably 99% by mass or more, and further preferably 99.5% by mass or more. The upper limit of purity is not particularly limited.

The yield of 1,2,4,5-cyclohexanetetracarboxylic acid is preferably 50% by mass, more preferably 60% by mass or more, even more preferably 65% by mass or more, and further preferably 70% by mass or more. The upper limit is not particularly limited, and is preferably 95% by mass or less from the viewpoint of production.

In the present invention, the average particle size of the 1,2,4,5-cyclohexanetetracarboxylic acid as a starting material is 20 μm or more. The use of cyclohexanetetracarboxylic acid having an average particle size of 20 μm or more results in a good dehydration rate.

The average particle size of cyclohexanetetracarboxylic acid is preferably 25 μm or more and more preferably 30 μm or more. The upper limit value of the average particle size of cyclohexanetetracarboxylic acid is not particularly limited, and may be, for example, 1000 μm or less, 500 μm or less, 300 μm or less, or 100 μm or less from the viewpoint of the easiness to put the starting material into a reaction vessel.

Here, as for the average particle size of cyclohexanetetracarboxylic acid, the lengths of the major axes of 100 particles on a 100× or 1000× image taken by a field emission-scanning electron microscope (FE-SEM) are measured using image processing software Image J. The average value of the resulting major axis lengths of the particles is regarded as the average particle size of cyclohexanetetracarboxylic acid.

In the present invention, the proportion of particles having a small particle size in the cyclohexanetetracarboxylic acid as a starting material is preferably small. Specifically, the proportion of particles having a particle size of 10 μm or less is preferably 20% by number or less, more preferably 15% by number or less, and even more preferably 10% by number or less.

Due to the proportion of particles having a particle size of 10 μm or less being within the above range, the production method can provide a better dehydration rate.

As for the proportion of cyclohexanetetracarboxylic acid particles having a particle size of 10 μm or less, the lengths of the major axes of 100 particles on a 100× or 1000× image taken by a field emission-scanning electron microscope (FE-SEM) are measured using image processing software Image J. Then, the proportion is determined from the resulting major axis lengths of the particles.

In the present invention, the proportion of particles having a large particle size in the cyclohexanetetracarboxylic acid as a starting material is preferably large. Specifically, the proportion of particles having a particle size of 40 μm or more is preferably 10% by number or more, more preferably 15% by number or more, even more preferably 20% by number or more, and further preferably 25% by number or more.

Due to the proportion of particles having a particle size of 40 μm or more being within the above range, the production method can provide a better dehydration rate.

As for the proportion of cyclohexanetetracarboxylic acid particles having a particle size of 40 μm or more, the lengths of the major axes of 100 particles on a 100× or 1000× image taken by a field emission-scanning electron microscope (FE-SEM) are measured using image processing software Image J. Then, the proportion is determined from the resulting major axis lengths of the particles.

In the present invention, the proportion of particles having a large particle size in the cyclohexanetetracarboxylic acid as a starting material is preferably large. Specifically, the proportion of particles having a particle size of 20 μm or more is preferably 35% by number or more, more preferably 45% by number or more, even more preferably 55% by number or more, further preferably 65% by number or more, and furthermore preferably 75% by number or more.

Due to the proportion of particles having a particle size of 20 μm or more being within the above range, the production method can provide a better dehydration rate.

As for the proportion of cyclohexanetetracarboxylic acid particles having a particle size of 20 μm or more, the lengths of the major axes of 100 particles on a 100× or 1000× image taken by a field emission-scanning electron microscope (FE-SEM) are measured using image processing software Image J. Then, the proportion is determined from the resulting major axis lengths of the particles.

The method for configuring cyclohexanetetracarboxylic acid to have the aforementioned average particle size and the aforementioned proportion of particles having a particle size of 20 μm or more, 40 μm or more, or 10 μm or less is not particularly limited, and is suitably selected from known methods and used.

A specific example is a method in which cyclohexanetetracarboxylic acid is sifted, and cyclohexanetetracarboxylic acid having a desired particle size range is used. When cyclohexanetetracarboxylic acid is produced by the nuclear hydrogenation reaction of pyromellitic acid, drying under mild conditions makes it possible to increase the average particle size and, moreover, reduce the proportion of particles having a particle size of 10 μm or less. Mild drying conditions mean mere heat drying, drying in a small amount of nitrogen stream, and the like. On the other hand, the use of a Flash Jet Dryer (manufactured by Seishin Enterprise Co., Ltd.) that instantaneously performs drying in a high-temperature/high-speed air stream or a Dry Meister (manufactured by Hosokawa Micron Corporation) that is a direct heating air flow dryer results in a small particle size, and it is thus preferable to avoid the use of such dryers in the present invention.

Cyclohexanetetracarboxylic acid that has a large average particle size and a small proportion of particles having a particle size of 10 μm or less may be obtained by performing a recrystallization treatment on cyclohexanetetracarboxylic acid. Specifically, acetic acid is preferably used as a solvent, the solution is stirred while being heated, then cooled, and subjected to solid-liquid separation, and thereby the target crystals are obtained.

Also, cyclohexanetetracarboxylic acid having a larger average particle size can be obtained from cyclohexanetetracarboxylic acid composed of particles having various particle sizes by utilizing the difference of dissolution rates resulting from the particle size to dissolve only small particles and performing solid-liquid separation. Specifically, cyclohexanetetracarboxylic acid is heated and stirred in a solvent (preferably acetic acid) to form a slurry in which small particles of cyclohexanetetracarboxylic acid are dissolved, the slurry retained in a high temperature state is subjected to solid-liquid separation as-is, and thereby cyclohexanetetracarboxylic acid having a larger average particle size can be obtained.

<Dehydrating Agent>

The dehydrating agent used in the present invention is not particularly limited, and is suitably selected from known dehydrating agents and used. Examples of known dehydrating agents include acetic anhydride, propionic anhydride, trifluoroacetic anhydride, succinic anhydride, maleic anhydride, benzoic anhydride, phthalic anhydride, acetyl chloride, phosphoric acid chloride, thionyl chloride, and phosgene. Among these, the dehydrating agent is preferably acetic anhydride from the viewpoint of economy and usability.

In the present invention, acetic anhydride is preferably used in an amount of 2.0 to 100 moles per mole of 1,2,4,5-cyclohexanetetracarboxylic acid.

From the viewpoint of obtaining a sufficient dehydration rate, acetic anhydride is preferably used in an amount of 2.0 moles or more, more preferably 2.5 moles or more, even more preferably 3 moles or more, and further preferably 4 moles or more, and from the viewpoint of economy and from the viewpoint of removing the dehydrating agent after reaction, acetic anhydride is preferably used in an amount of 100 moles or less, more preferably 75 moles or less, even more preferably 50 moles or less, and further preferably 25 moles or less.

In the present invention, acetic anhydride used as a dehydrating agent is a liquid and thus also functions as a solvent.

<Dehydration Reaction Conditions>

In the present invention, cyclohexanetetracarboxylic acid is subjected to a dehydration reaction (also referred to as an anhydration reaction) in a slurry state in the presence of a dehydrating agent. The slurry state means that the cyclohexanetetracarboxylic acid as a starting material does not completely dissolve in a dehydrating agent and an optionally added solvent and partially exists in a solid state and, also, the produced acid anhydride does not completely dissolve in the dehydrating agent and the optionally added solvent and partially exists in a solid state. Accordingly, a state where either the starting material or the product or both partially exist in a solid state in the reaction system is referred to as a slurry state.

From the viewpoint of promoting dissolution of cyclohexanetetracarboxylic acid in a solvent to promote the dehydration reaction of cyclohexanetetracarboxylic acid, the reaction temperature of the dehydration reaction is preferably 80° C. or more, more preferably 90° C. or more, and even more preferably 95° C. or more. From the viewpoint of suppressing the decomposition of the starting material and the product and the volatilization of a dehydrating agent and a solvent, which will be described below, and preventing the product from caking after lowering the temperature, the reaction temperature in the dehydration reaction is preferably 150° C. or less, more preferably 140° C. or less, even more preferably 130° C. or less, and further preferably 120° C. or less.

The dehydration reaction may involve only heating the slurry of cyclohexanetetracarboxylic acid and a dehydrating agent, or may involve heating the dehydrating agent to reflux.

The dehydration reaction is preferably carried out in an atmosphere of an inert gas such as nitrogen gas.

<Solvent>

In the present invention, it is also preferable to carry out the dehydration reaction in the presence of a dehydrating agent and a solvent.

The solvent is not particularly limited, and acetic acid (also referred to as glacial acetic acid) is preferably used as a solvent. Acetic acid is preferably used in an amount of 0.5 to 10 times by volume and more preferably 1 to 5 times by volume based on the dehydrating agent.

In addition to acetic acid, a hydrocarbon, a halogenated hydrocarbon, an ester, a ketone, an ether, a fatty acid, or the like having a boiling point of 50° C. or more may be added as a solvent.

<Dehydration Rate>

In the present invention, the dehydration rate of the 1,2,4,5-cyclohexanetetracarboxylic acid as a starting material is preferably 98.0% or more, more preferably 98.5% or more, even more preferably 99.0% or more, and particularly preferably 99.3% or more.

Due to the dehydration rate being within the above range, cyclohexanetetracarboxylic dianhydride having excellent purity can be obtained.

The dehydration rate is measured by the method described in the Examples.

<Step of Recovering Cyclohexanetetracarboxylic Dianhydride>

In the present invention, it is preferable that the method further includes the step of recovering cyclohexanetetracarboxylic dianhydride (hereinafter also simply referred to as a recovery step).

After the dehydration reaction of cyclohexanetetracarboxylic acid, the reaction solution is cooled to room temperature to precipitate crystals of cyclohexanetetracarboxylic dianhydride, which are subjected to solid-liquid separation, and thereby cyclohexanetetracarboxylic dianhydride can be obtained. The use of acetic anhydride as a dehydrating agent and the use of acetic acid as a solvent result in an increased amount of precipitated crystals and are thus industrially advantageous. Crystals of cyclohexanetetracarboxylic dianhydride separated by solid-liquid separation are preferably dried in a suitable manner.

The mother liquor from which the crystals have been separated may be recycled. Whether the mother liquor should be returned to the reaction vessel for a dehydration reaction is determined according to the extent of impurity buildup in the system.

EXAMPLES

The present invention will be described in more detail by way of Examples and Comparative Examples below, but the present invention is not limited to these Examples.

Preparation Example 1-1

First, 390.1 kg of pyromellitic acid, 2340.9 kg of water, 131.0 kg of a 5% by mass Pd-carbon powder catalyst (manufactured by N.E. Chemcat Corporation, a product wetted with water, PE-type, a water content of 55% by mass), and 56.2 kg of a 5% by mass Rh-carbon powder catalyst (manufactured by N.E. Chemcat Corporation, a product wetted with water, a water content of 50% by mass) were charged into a 3.86 m$^3$ SUS316L reaction vessel equipped with a thermocouple, a stirrer, a temperature controller, and the like. While stirring the mixture, hydrogen was fed to 8 MPa, and the temperature was raised to 50° C. While retaining the pressure and the temperature, the hydrogenation reaction was continued until the molar amount of absorbed hydrogen was 3 times the molar amount of pyromellitic acid charged. The resulting reaction solution was discharged, the catalyst was separated by filtration, and thus a colorless, transparent filtrate was obtained.

Thereafter, the resulting filtrate was concentrated until the concentration of nuclear-hydrogenated pyromellitic acid was 33% by mass, and then cooled to 20° C. to precipitate crystals of 1,2,4,5-cyclohexanetetracarboxylic acid. The precipitated crystals were separated by filtration.

The resulting crystals of 1,2,4,5-cyclohexanetetracarboxylic acid were charged into a 2.5 m$^3$ SUS316 conical dryer, and the crystals were dried at 40° C. for 16 hours and then further dried at 90° C. for 29 hours (total 45 hours) to obtain white crystals.

The particle size of the resulting 1,2,4,5-cyclohexanetetracarboxylic acid measured by SEM observation revealed an average particle size of 33.4 µm. The proportion of particles having a particle size of 10 µm or less was 5% by number, the proportion of particles having a particle size of 20 µm or more was 82% by number, and the proportion of particles having a particle size of 40 µm or more was 28% by number.
<Measurement of Average Particle Size, Proportion of Particles Having a Particle Size of 10 µm or Less, Proportion of Particles Having a Particle Size of 40 µm or More, and Proportion of Particles Having a Particle Size of 20 µm or More>

The lengths of the major axes of particles on a 100× or 1000× image taken by FE-SEM (manufactured by Hitachi High-Technologies Corporation, S-3000N, voltage of 10 kV) were measured using image processing software Image J. Measurement was made on 100 particles, and the average value of the obtained results was regarded as the average particle size of cyclohexanetetracarboxylic acid. Also, the proportion of particles having a particle size (major axis length) of 10 µm or less, the proportion of particles having a particle size of 20 µm or more, and the proportion of particles having a particle size (major axis length) of 40 µm or more were calculated.

Preparation Example 1-2

First, 100 g of 1,2,4,5-cyclohexanetetracarboxylic acid (average particle size: 33.4 µm) obtained in Preparation Example 1-1 and 283.37 g of acetic acid were charged into a 500 mL four-neck glass flask equipped with a thermocouple, a stirrer, and a temperature controller, the temperature was raised to 100° C. while stirring the mixture, and stirring was continued at 100° C. for 5 hours after completing the temperature increase.

Without being cooled, the resulting slurry was subjected to solid-liquid separation by suction filtration using quantitative filter paper No. 5B (manufactured by ADVANTEC Group) at a temperature close to 100° C. The resulting wet crystals of 1,2,4,5-cyclohexanetetracarboxylic acid were dried in a dryer at 130° C. for 3 hours in a nitrogen stream while feeding nitrogen at 1 L/min, and thereby white crystals of 1,2,4,5-cyclohexanetetracarboxylic acid were obtained.

From SEM observation of the resulting white crystals, the average particle size was 46.0 µm. The proportion of particles having a particle size of 10 µm or less was 2% by number, the proportion of particles having a particle size of 20 µm or more was 81% by number, and the proportion of particles having a particle size of 40 µm or more was 45% by number.

Preparation Example 1-3

First, 390.1 kg of pyromellitic acid, 2340.9 kg of water, 131.0 kg of a 5% by mass Pd-carbon powder catalyst (manufactured by N.E. Chemcat Corporation, a product wetted with water, PE-type, a water content of 55% by mass), and 56.2 kg of a 5% by mass Rh-carbon powder catalyst (manufactured by N.E. Chemcat Corporation, a product wetted with water, a water content of 50% by mass) were charged into a 3.86 m$^3$ SUS316L reaction vessel equipped with a thermocouple, a stirrer, a temperature controller, and the like. While stirring the mixture, hydrogen was fed to 8 MPa, and the temperature was raised to 50° C. While retaining the pressure and the temperature, the hydrogenation reaction was continued until the molar amount of absorbed hydrogen was 3 times the molar amount of pyromellitic acid charged. The resulting reaction solution was discharged, the catalyst was separated by filtration, and thus a colorless, transparent filtrate was obtained.

Thereafter, the resulting filtrate was concentrated until the concentration of nuclear-hydrogenated pyromellitic acid was 33% by mass, and then cooled to 20° C. to precipitate crystals of 1,2,4,5-cyclohexanetetracarboxylic acid. The precipitated crystals were separated by filtration.

The resulting crystals of 1,2,4,5-cyclohexanetetracarboxylic acid were charged into a Flash Jet Dryer (manufactured by Seishin Enterprise Co., Ltd.), and the crystals were dried under conditions having a starting material feeding rate of 55 kg/h, an inlet temperature of 170° C., an outlet temperature of 110° C., a starting material temperature of 12.4° C., a discharge air volume of 6.8 Nm$^3$/min, and a discharge pressure of 53 kPa, and thereby white crystals of 1,2,4,5-cyclohexanetetracarboxylic acid were obtained.

The particle size of the resulting white crystals of 1,2,4,5-cyclohexanetetracarboxylic acid measured by SEM observation revealed an average particle size of 6.9 µm. The proportion of particles having a particle size of 10 µm or less was 81% by number, the proportion of particles having a particle size of 20 µm or more was 3.2% by number, and the proportion of particles having a particle size of 40 µm or more was 0% by number.

Preparation Example 1-4

First, 100 g of 1,2,4,5-cyclohexanetetracarboxylic acid (average particle size: 6.9 µm) obtained in Preparation Example 1-3 and 283.37 g of acetic acid were charged into a 500 mL four-neck glass flask equipped with a thermocouple, a stirrer, and a temperature controller, the temperature was raised to 100° C. while stirring the mixture, and stirring was continued at 100° C. for 5 hours after completing the temperature increase.

Without being cooled, the resulting slurry was subjected to solid-liquid separation by suction filtration using quantitative filter paper No. 5B (manufactured by ADVANTEC Group) at a temperature close to 100° C. The resulting wet crystals of 1,2,4,5-cyclohexanetetracarboxylic acid were dried in a dryer at 130° C. for 3 hours in a nitrogen stream fed at 1 L/min, and thereby white crystals of 1,2,4,5-cyclohexanetetracarboxylic acid were obtained.

From SEM observation of the resulting white crystals, the average particle size was 17.3 μm. The proportion of particles having a particle size of 10 μm or less was 24% by number, the proportion of particles having a particle size of 20 μm or more was 32% by number, and the proportion of particles having a particle size of 40 μm or more was 3% by number.

Preparation Example 2-1

First, 390.1 kg of pyromellitic acid, 2340.9 kg of water, 131.0 kg of a 5% by mass Pd-carbon powder catalyst (manufactured by N.E. Chemcat Corporation, a product wetted with water, PE-type, a water content of 55% by mass), and 56.2 kg of a 5% by mass Rh-carbon powder catalyst (manufactured by N.E. Chemcat Corporation, a product wetted with water, a water content of 50% by mass) were charged into a 3.86 m$^3$ SUS316L reaction vessel equipped with a thermocouple, a stirrer, a temperature controller, and the like. While stirring the mixture, hydrogen was fed to 8 MPa, and the temperature was raised to 50° C. While retaining the pressure and the temperature, the hydrogenation reaction was continued until the molar amount of absorbed hydrogen was 3 times the molar amount of pyromellitic acid charged. The resulting reaction solution was discharged, the catalyst was separated by filtration, and thus a colorless, transparent filtrate was obtained.

Thereafter, the resulting filtrate was concentrated at 100° C. until the concentration of nuclear-hydrogenated pyromellitic acid was 27.2% by mass, and then cooled to 20° C. to precipitate crystals of 1,2,4,5-cyclohexanetetracarboxylic acid. The precipitated crystals were separated by filtration.

The resulting crystals of 1,2,4,5-cyclohexanetetracarboxylic acid were charged into a 2.5 m$^3$ SUS316 conical dryer, and the crystals were dried at 40° C. for 16 hours and then further dried at 90° C. for 29 hours (total 45 hours) to obtain white crystals.

The resulting 1,2,4,5-cyclohexanetetracarboxylic acid was evaluated as follows.

<Measurement of H-PMA Purity (Trimethyl Phosphate Method)>

The purity of 1,2,4,5-cyclohexanetetracarboxylic acid (hereinafter also referred to as H-PMA) in the resulting crystals (the H-PMA purity) was measured as follows.

Specifically, 0.10 g of the resulting crystals were placed in a test tube, then 3.0 g of triethylammonium chloride (manufactured by Wako Pure Chemical Industries, Ltd.) and 10 ml of trimethyl phosphate (manufactured by Kishida Chemical Co., Ltd.) were added, and the mixture was heated in a block heater at 180° C. for 90 minutes to carry out an esterification treatment.

After being cooled to room temperature, the mixture was completely dissolved in 15 ml of chloroform, ion-exchange water was further added to carry out a liquid separation treatment, and the resulting chloroform solution was subjected to a gas chromatography analysis. The H-PMA purity was calculated by a simple area method.

(Gas Chromatography Analysis Conditions)

Gas chromatography analyzer: 6890N (manufactured by Agilent Technologies, Inc.)

Capillary column: DB-1 (manufactured by Agilent Technologies, Inc.)

Injection temperature: 300° C.

Detection temperature: 290° C.

Initial column temperature, retention time: 200° C., 10 min

Heating rate: 7° C./min

Final column temperature, retention time: 280° C., 15 min

Carrier gas: Helium

Linear velocity of carrier gas: 41 cm/sec

Detector: FID

<Method for Calculating Yield>

The total yield of step 1 and step 2 was obtained by multiplying the mass of crystals obtained by crystal precipitation (step 2) by the H-PMA purity, then dividing the resulting value by the value obtained by multiplying the mass of the aqueous H-PMA solution charged (the mass of the H-PMA-containing aqueous solution used in step 1) by the H-PMA concentration in the aqueous solution, and multiplying the resulting value by 100. That is, the total yield can be expressed by the following equation.

Yield (%)={(Mass (g) of crystals obtained by crystal precipitation)×(H-PMA purity (%) in crystals)}/{(Mass (g) of aqueous H-PMA solution charged)×(H-PMA concentration (%) in the aqueous solution)}×100

The method for analyzing the H-PMA concentration in the H-PMA-containing aqueous solution used in step 1 (the aqueous H-PMA solution charged) is provided below.

Specifically, 0.60 g of the H-PMA-containing aqueous solution (having a concentration of 5 to 30% by mass) was placed in a test tube, then 3.0 g of triethylammonium chloride (manufactured by Wako Pure Chemical Industries, Ltd.) and 10 ml of trimethyl phosphate (manufactured by Kishida Chemical Co., Ltd.) were added, and the mixture was heated in a block heater at 180° C. for 45 minutes and removed from the block heater once. Thereafter, 10 ml of trimethyl phosphate (manufactured by Kishida Chemical Co., Ltd.) was added again, and the mixture was further heated in a block heater at 180° C. for 90 minutes to carry out an esterification treatment.

Thereafter, 0.10 g of triphenylmethane (manufactured by Tokyo Chemical Industry Co., Ltd.) was added as an internal standard, the mixture was completely dissolved in 15 ml of chloroform, ion-exchanged water was further added to carry out a liquid separation treatment, and the resulting chloroform solution was subjected to a gas chromatography analysis. The H-PMA concentration was calculated by an internal standard method using triphenylmethane as an internal standard.

(Gas Chromatography Analysis Conditions)

Gas chromatography analyzer: 6890N (manufactured by Agilent Technologies, Inc.)

Capillary column: DB-1 (manufactured by Agilent Technologies, Inc.)

Injection temperature: 300° C.

Detection temperature: 290° C.

Initial column temperature, retention time: 160° C., 20 min

Heating rate: 10° C./min

Final column temperature, retention time: 280° C., 15 min

Carrier gas: Helium

Carrier gas pressure: 33.1 kPa

Detector: FID

Preparation Examples 2-2 to 2-4

Crystals of 1,2,4,5-cyclohexanetetracarboxylic acid were obtained in the same manner as in Preparation Example 2-1 except that the filtrate was concentrated at 100° C. until the concentration of nuclear-hydrogenated pyromellitic acid reached the concentration shown in Table 2.

The purity and the yield of the resulting 1,2,4,5-cyclohexanetetracarboxylic acid crystals were measured in the same manner as in Preparation Example 2-1.

The results are shown in Table 2 below.

TABLE 2

| | Preparation Example | | | |
|---|---|---|---|---|
| | 2-1 | 2-2 | 2-3 | 2-4 |
| Concentration (% by mass) of concentrate | 27.2 | 30.7 | 32.8 | 33.8 |
| Purity (% by mass) of 1,2,4,5-cyclohexanetetracarboxylic acid crystals | 99.1 | 99.6 | 99.6 | 99.5 |
| Yield (% by mass) of 1,2,4,5-cyclohexanetetracarboxylic acid | 45.7 | 66.3 | 72.2 | 74.4 |

As shown in Table 2, an aqueous solution containing 1,2,4,5-cyclohexanetetracarboxylic acid was concentrated such that the concentration of the concentrate was 29% by mass or more and 34% by mass or less, then the concentrate was cooled to obtain 1,2,4,5-cyclohexanetetracarboxylic acid crystals, and thereby it was possible to recover 1,2,4,5-cyclohexanetetracarboxylic acid having excellent purity in a high yield. On the other hand, in Preparation Example 2-1 in which the concentration of the concentrate was less than 29% by mass, the yield of the resulting 1,2,4,5-cyclohexane was low.

Example 1

First, 47.5 g (0.18 mol) of 1,2,4,5-cyclohexanetetracarboxylic acid having an average particle size of 33.4 μm obtained in Preparation Example 1-1, 55.4 g (0.542 mol, 3.0 moles per mole of cyclohexanetetracarboxylic acid added) of acetic anhydride, and 134.6 g (2.5 times the volume of acetic anhydride) of acetic acid were charged into a 500 mL four-neck glass flask equipped with a thermocouple, a Dimroth condenser, and a stirrer, and the system was replaced with nitrogen gas while stirring the mixture. Subsequently, the temperature was raised to 100° C. while allowing nitrogen gas to flow at 100 mL/min to carry out a dehydration reaction of cyclohexanetetracarboxylic acid at 100° C. for 2 hours. After the reaction, the temperature was lowered to room temperature to precipitate crystals, and then the crystals were separated. The resulting crystals were rinsed with 13.1 g of acetic anhydride and then dried to measure the dehydration rate.

The dehydration reaction carried out in the Examples was as follows. The results are shown in Table 3 below.

[Formula 2]

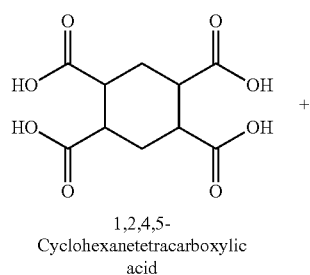

1,2,4,5-Cyclohexanetetracarboxylic acid

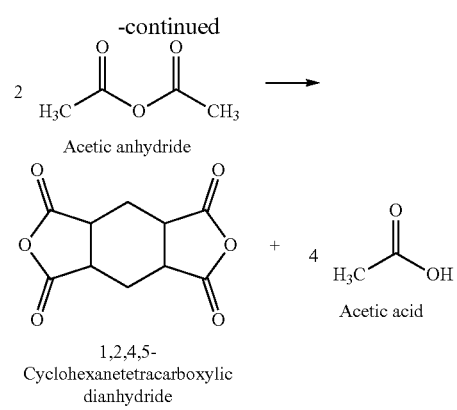

Example 2, and Comparative Examples 1 and 2

The dehydration reaction of cyclohexanetetracarboxylic acid was carried out in the same manner as in Example 1 to measure the dehydration rate except that cyclohexanetetracarboxylic acid obtained in Preparation Examples 1-2, 1-3, or 1-4 was used. The results are shown in Table 3 below.

TABLE 3

| | Example | | Comparative Example | |
|---|---|---|---|---|
| | 1 | 2 | 1 | 2 |
| Average particle size (μm) | 33.4 | 46.0 | 6.9 | 17.3 |
| Proportion (% by number) of particles having a particle size of 10 μm or less | 5 | 2 | 81 | 24 |
| Proportion (% by number) of particles having a particle size of 20 μm or more | 82 | 81 | 3 | 32 |
| Proportion (% by number) of particles having a particle size of 40 μm or more | 28 | 45 | 0 | 3 |
| Reaction temperature (° C.) | 100 | 100 | 100 | 100 |
| Dehydration rate (%) | 99.7 | 99.4 | 96.7 | 97.8 |

<Measurement of Dehydration Rate>

As for the dehydration rate of cyclohexanetetracarboxylic acid, a sample was analyzed by liquid chromatography to quantify the 1,2,4,5-cyclohexanetetracarboxylic acid as a starting material, and then the dehydration rate (%) defined by the following equation 1 was calculated.

Dehydration rate (%)=100−Amount (% by mass) of cyclohexanetetracarboxylic acid in sample   Equation 1

(Pretreatment Conditions for Liquid Chromatography)

First, 2 g of a sample was precisely weighed, 100 ml of dehydrated methanol was added, the mixture was heated to reflux for 1 hour to carry out a methyl esterification reaction, and thereby a liquid chromatography sample was prepared.

Provided that, in this pretreatment, only the cyclohexanetetracarboxylic dianhydride in the sample is esterified, and the 1,2,4,5-cyclohexanetetracarboxylic acid as a reaction starting material in the sample is not esterified.

(Liquid Chromatography Analysis Conditions)

The liquid chromatography analysis conditions were as follows.

Liquid chromatography analyzer: LC-6AD (solvent delivery unit), CTO-10A (constant temperature chamber), SCL-10A (UV), SPD-10AV (UV-VIS detector), SPD-M20A (PDA detector)

Column: Shodex RSpak DE-413L
Detector: UV (210 nm)
Eluent composition: Solution A=Acetonitrile, Solution B=0.5% Aqueous phosphoric acid solution
Mode: Binary gradient
Flow rate: 1.0 ml/min
Temperature of constant temperature chamber: 35° C.

The eluent conditions were as follows. The eluent had solution A:solution B=10:90 (volume ratio) at an analysis time of 0 to 15 minutes, and a gradient of solution A:solution B=from 10:90 (volume ratio) to 50:50 (volume ratio) was created at 15 to 20 minutes. Moreover, a gradient of solution A:solution B=from 50:50 (volume ratio) to 80:20 (volume ratio) was created at an analysis time of 20 to 25 minutes. The ratio was retained at solution A:solution B=80:20 (volume ratio) until at 40 minutes, then a gradient of solution A:solution B=from 80:20 (volume ratio) to 10:90 (volume ratio) was created at an analysis time of 40 to 50 minutes, and the ratio was retained at solution A:solution B=10:90 (volume ratio) until at 70 minutes.

In the above liquid chromatography, cyclohexanetetracarboxylic acid was measured, wherein the amount of cyclohexanetetracarboxylic acid in a sample was quantified by an absolute calibration method to determine the mass proportion of cyclohexanetetracarboxylic acid in the sample, and the resulting value was subtracted from 100 to obtain a dehydration rate.

That is, when 2 g of unreacted cyclohexanetetracarboxylic acid is contained in a 100 g sample, the dehydration rate is 98%.

INDUSTRIAL APPLICABILITY

As described above, according to the production method of the present invention, cyclohexanetetracarboxylic dianhydride can be stably obtained at a high dehydration rate.

The cyclohexanetetracarboxylic dianhydride obtained by the present invention has high purity and is thus expected to be used as a starting material of polyimides, epoxy resin curing agents, solder resists, and the like.

The invention claimed is:

1. A method for producing 1,2,4,5-cyclohexanetetracarboxylic dianhydride, comprising:
   subjecting 1,2,4,5-cyclohexanetetracarboxylic acid to a dehydration reaction in a slurry state in the presence of a dehydrating agent, wherein
   an average particle size of the 1,2,4,5-cyclohexanetetracarboxylic acid is 33.4 µm or more.

2. The method according to claim 1, wherein in the 1,2,4,5-cyclohexanetetracarboxylic acid, a proportion of particles having a particle size of 10 µm or less is 20% by number or less.

3. The method according to claim 1, wherein in the 1,2,4,5-cyclohexanetetracarboxylic acid, a proportion of particles having a particle size of 40 µm or more is 20% by number or more.

4. The method according to claim 1, wherein in the 1,2,4,5-cyclohexanetetracarboxylic acid, a proportion of particles having a particle size of 20 µm or more is 35% by number or more.

5. The method according to claim 1, wherein a dehydration rate of the 1,2,4,5-cyclohexanetetracarboxylic acid is 98% or more.

6. The method according to claim 1, wherein a reaction temperature of the dehydration reaction is 80 to 150° C.

7. The method according to claim 1, wherein the dehydrating agent is acetic anhydride.

8. The method according to claim 7, wherein the acetic anhydride is used in an amount of 2.0 to 100 moles per mole of the 1,2,4,5-cyclohexanetetracarboxylic acid.

9. The method according to claim 1, wherein the dehydration reaction of the 1,2,4,5-cyclohexanetetracarboxylic acid is carried out in the presence of the dehydrating agent and a solvent.

10. The method according to claim 9, wherein the solvent is acetic acid.

* * * * *